United States Patent [19]
Daikuzono

[11] Patent Number: 5,129,897
[45] Date of Patent: Jul. 14, 1992

[54] CURVED LASER LIGHT EMITTER

[75] Inventor: Norio Daikuzono, Chiba, Japan

[73] Assignee: S.L.T. Japan Co., Ltd., Tokyo, Japan

[21] Appl. No.: 478,195

[22] Filed: Feb. 12, 1990

[30] Foreign Application Priority Data

Feb. 15, 1989 [JP] Japan ................................ 1-35841

[51] Int. Cl.$^5$ ............................................ A61B 17/32
[52] U.S. Cl. ........................................................ 606/16
[58] Field of Search ................................ 606/13-16; 128/395-398

[56] References Cited

U.S. PATENT DOCUMENTS

| | | | |
|---|---|---|---|
| 3,834,391 | 9/1974 | Block | 606/16 |
| 4,126,136 | 11/1978 | Auth et al. | 128/303.1 |
| 4,233,493 | 11/1980 | Nath | 128/397 |
| 4,273,127 | 6/1981 | Auth et al. | 128/303.1 |
| 4,461,283 | 7/1984 | Doi | 606/15 |
| 4,693,244 | 9/1987 | Daikuzono | 128/398 |
| 4,736,743 | 4/1988 | Daikuzono | 128/303.1 |
| 4,799,479 | 1/1989 | Spears | 128/303.1 |
| 4,832,979 | 5/1989 | Hoshino | 427/38 |
| 4,848,339 | 7/1989 | Rink et al. | 128/398 |
| 4,860,743 | 8/1989 | Abela | 606/15 |

FOREIGN PATENT DOCUMENTS

| | | | |
|---|---|---|---|
| 0069351 | 1/1983 | European Pat. Off. | 606/16 |
| 2185188 | 7/1987 | United Kingdom . | |

*Primary Examiner*—Max Hindenburg
*Attorney, Agent, or Firm*—Lowe, Price, Le Blanc & Becker

[57] ABSTRACT

A laser light emitter used in a medical treatment has an optical fiber which extends in a longitudinal direction and at the fore end portion thereof. The core of the fore end portion is not surrounded by a clad but exposed to serve as a laser light emitting portion. A holder supports the optical fiber. Part of or the whole of the emitting portion bends at a certain angle on a longitudinal cross section of the extending direction of the optical fiber. To ensure fixing of the optical fiber to the holder, the optical fiber preferably has a circular cross section, and the holder comprises a thin plate with a concave shaped recess along the edge to which the optical fiber is mounted. The optical fiber extends along the inner surface of the concave shaped recess along the edge of the holder and is fixed thereto by a heat resistant adhesive. To use the emitter in surgery, the holder is connected to a fore end of a hand piece held by an operator. The holder substantially supports the exposed core portion of the optical fiber and a base portion of the optical fiber.

18 Claims, 4 Drawing Sheets

CURVED LASER LIGHT EMITTER

BACKGROUND OF THE INVENTION

This invention relates to a laser light emitter to permit an incision, a vaporization of living tissue of animal organisms, or a thermal therapy in case of surgical and internal medical treatments.

Medical treatments such as incisions of living tissue of animal organisms by irradiation with laser light are conspicuous due to the ability of hemostasis during such treatments. It had been the conventional method that the laser light was irradiated from the fore end portion of an optical fiber system which is non-contact with the living tissue, but this method causes severe damage to the fore end portion of the optical fiber. Therefore, a method which has been utilized lately is as follows; at first, the laser light, after being transmitted into an optical fiber system, is fed into an emitting member of a probe being in contact or non-contact with the living tissue (hereafter "living tissue" is sometimes expressed by "tissue" only). Then the laser light emitted from the surface of the probe is irradiated on the tissue.

On the other hand, U.S. Pat. No. 4,273,127 discloses a method of an incision for treated tissue with a laser light emitter comprising a light guide having the form of a knife and a relatively narrow working edge and an optical fiber fixed to a back of the light guide. The treated tissue is incised by the laser light which passes from a tip of the optical fiber through the light guide to the narrow working edge and irradiates from the edge. In this case, the contact between the working edge and the tissue provides tactile feedback to an operator like feedback obtained in mechanical incision.

However, according to this method, a structural distance between the tip of the optical fiber and the working edge causes serious power loss. Therefore, a high output power level of a laser light generator is required.

Moreover, it requires a high accuracy to produce the emitter of this method so that an emitting direction of the laser light from the tip of the optical fiber meets the working edge of the light guide. The emitter is composed of two members; optical fiber and light guide. Accordingly, it is very expensive to produce the emitter.

Further, after being fed into the light guide, the laser light is scattered therein and emitted therefrom. Then, the rate of the laser light emission from the working edge is reduced. Therefore, the laser light generator should have a high output power level for sufficient incisions.

Moreover, the power of the laser light is concentrated on the working edge which meets a center line of a direction oriented by the tip of the optical fiber. And the rate of the laser light emitted from surrounding part of the working edge is extremely reduced. Accordingly, the ability of an incision is influenced by a small change of an angle between a light guide and the incised tissue. As a result, a surgery using this emitter can not be carried smoothly.

OBJECTS OF THE INVENTION

It is an object of the present invention to provide a laser light emitter permitting laser light power to be used effectively.

It is another object of the present invention to provide a laser light emitter permitting laser light emission from a wide surface area thereof.

It is another object of the present invention to provide a laser light emitter which can be produced at low costs. Because the laser light emitter has a simple composition; a laser light emitting portion is optical fiber itself.

Other and further objects, features and advantages of the present invention will appear more fully from the following description.

SUMMARY OF THE INVENTION

The present invention features a laser light emitter comprising an optical fiber which extends in a longitudinal direction, wherein the fore end portion of the optical fiber core is not surrounded by a clad but is exposed to emit laser light. A holder supports the optical fiber. Part of or the whole of the emitting portion bends at a certain angle on a longitudinal cross section of the extending direction of the optical fiber.

In the preferred embodiment of the present invention, the optical fiber has a circular cross section, the holder has the form of a thin plate and a concave recess shaped cross section at an optical fiber side edge of the holder, the optical fiber extends along the inner surface of the concave recess shaped optical fiber side edge of the holder and is fixed thereto by a heat resistant adhesive.

In the further preferred embodiment, the holder is connected to a fore end of a hand piece held by an operator, and the holder substantially supports an exposed core portion of the optical fiber. The hand piece also supports a base portion of the optical fiber.

In the further preferred embodiment, the exposed core portion and at least a core portion side of the holder are formed to be the thinner, at the nearer part to a tip end longitudinally.

In the further preferred embodiment, the holder has the form of a thin plate and forms a knife at a side opposite to the optical fiber side thereof.

In the further preferred embodiment, said optical fiber is covered with a surface layer containing laser light absorbing particles, laser light scattering particles having a larger refractive index than that of the material of the core and a binder made from a laser light transmissible material on at least the exposed surface of the bending portion of the optical fiber.

In the further preferred embodiment, at least the exposed surface of the bending portion of the optical fiber is roughened and said surface layer is formed on said roughened surface.

DETAILED DESCRIPTION OF THE INVENTION

According to the present invention, this emitter has an optical fiber which extends in a longitudinal direction, and at the fore end thereof, whose core is not surrounded by a clad but exposed to be an emitting portion and a holder which supports the optical fiber. Previously, in case of a straight optical fiber, the laser light is emitted from the tip end of the optical fiber. However, according to the present invention, the part or whole of the exposed core portion of the optical fiber bends at a certain angle on a longitudinal cross section of its extending direction such that the laser light is emitted from the bending portion of the optical fiber.

Moreover, if a surface layer is formed on the surface of the exposed core portion, most of the laser light is emitted not from the tip end of the core, but from the surface layer, due to scattering of the laser light at the surface layer. Therefore, if an emitter having a surface layer formed on a suitable area of the exposed core portion is prepared in advance, the laser light can be emitted from an desired area of the exposed core portion in accordance with a specific purpose of a medical treatment Further, since the laser light transmitted in the optical fiber is emitted from the optical fiber itself, laser light power is used very efficiently. As a result, the laser light generator is not required to have a high output power level.

Now, the present invention is described more particularly.

Figure 1:
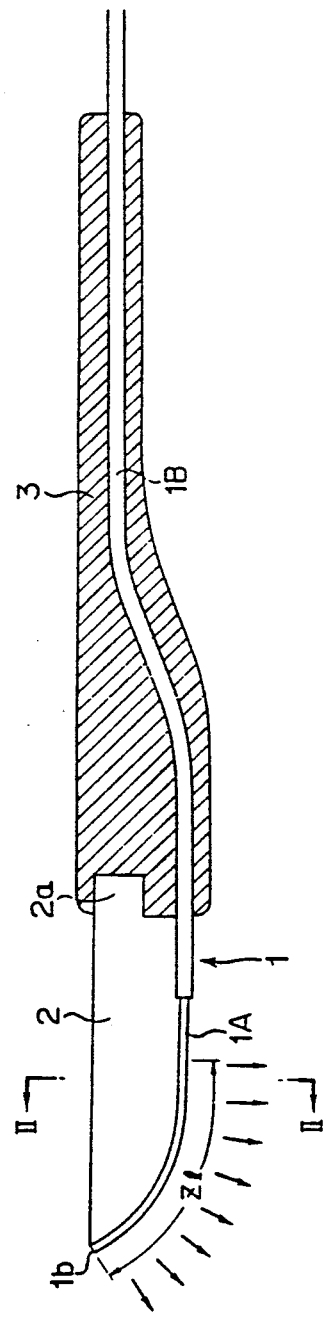
FIG. 1 is an elevational view of an embodiment of a laser light emitter relating to the present invention.

FIG. 1 shows a representative embodiment of a laser light emitter relating to the present invention. The emitter comprises an optical fiber 1, a holder 2 supporting the optical fiber 1 and a hand piece 3 which is connected to the holder 2 and held by an operator.

The holder 2 is fixed to the hand piece 3 by, for example, pressing of a connecting portion 2a of the holder 2 into the hand piece 3 and using an adhesive as supplement between mating surfaces. As is generally known, the optical fiber 1 comprises a core and a clad. However at the fore end portion of the optical fiber 1, the core is not surrounded by the clad but exposed to be an exposed core portion 1A. At the base portion of the optical fiber 1, the core is surrounded by the clad. Further, the surface of the clad can be surrounded by a protecting tube (not shown) as required.

Figure 2:
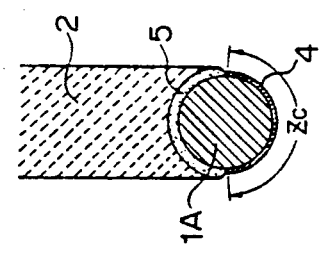
FIG. 2 is a cross sectional view taken on line II—II of FIG. 1.

The core portion 1A extends approximately ⅛ the length of an optical fiber side edge of the holder 2 from a tip end thereof. The rest of the optical fiber 1; i.e., the base of the optical fiber 1, is surrounded by the clad 1B. The core portion 1A is fixed to the optical fiber side edge of the holder 2. An example of a fixing method is shown in FIG. 2. The optical fiber side edge of the holder 2 has a concave recess having a circular arc shaped cross section of the extending direction of the optical fiber 1. The core portion 1A is fixed along to the inner surface of the concave recess. Then heat resistant adhesive 5 is applied to the mating surface of the holder 2 and the core portion 1A.

The base portion of the optical fiber 1 extends along the inside or the edge of the hand piece 3 and projects from the hand piece 3. Then, this projected optical fiber 1 is connected to a laser light generator optically. A controller for adjusting the laser light power is provided on the hand piece 3 or between the hand piece 3 and the laser light generator.

The fore end portion of the core portion 1A heads at a certain angle on a longitudinal cross section of the extending direction of the core portion 1A. In FIG. 2, this longitudinal cross section is a plane of this paper. In FIG. 1, the core portion 1A curves from the horizontal direction to an upper left direction on a plane of this paper. A surface layer 4 is formed at Z1 area in the extending direction as shown in FIG. 1 and at Zc area of a circumference of the core portion on the cross section as shown in FIG. 2.

Figure 3:
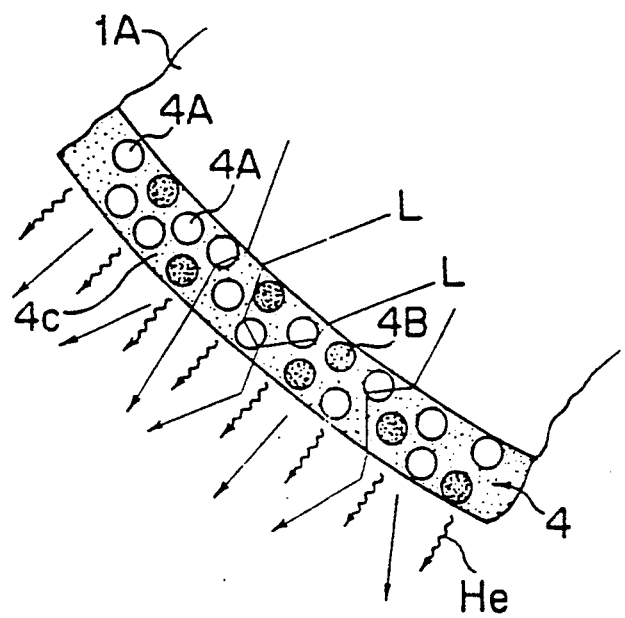
FIGS. 3 and 4 are schematic enlarged sectional views showing embodiments of surface layers and of laser light emission.

As shown in FIG. 3, the core portion 1A is covered with the surface layer 4 which contains light scattering particles 4A made of sapphire and the like having a larger refractive index than that of the core portion 1A. While the laser light L emitted from the surface of the core portion 1A passes through the surface layer 4, the laser light L, which impinges on the light scattering particle 4A, is partially reflected on the surface of the light scattering particle 4A or is partially penetrates into and is emitted from the particle 4A with refraction. Therefore, the laser light L is emitted in various directions from the entire surface layer 4. This produces a broad area of laser light irradiation.

Further, the surface layer 4 contains laser light absorbing particles 4B made of carbon and the like. Accordingly, when the laser light L impinges on the laser light absorbing particle 4B, the greater part of the energy of the laser light L is converted to heat energy He by means of the laser light absorbing particle 4B, and the tissue is heated by the heat energy from the surface layer 4.

By so doing, as the vaporization of the tissue is accelerated, the tissue can be incised with a low energy of the laser light from the core portion 1A. Therefore, when the tissue is incised, the laser light emitter of the present invention can be moved rapidly. Further, the required energy of the laser light penetrating into the core portion 1A is low. As a result, the surgery can be carried in short time, further with a cheap and small scaled laser light generator.

On the other hand, referring to forming of the surface layer 4, for example, if a dispersion containing said laser light absorbing particles 4B and light scattering particles 4A is coated on the surface of the core portion 1A, after a vaporization of a dispersion medium, the contact of an emitter having the surface layer with the tissue or other substances causes damage to the surface layer 4 very easily. Because said both kinds of particles are attached to the surface of the core portion 1A only by physical adsorptive power.

Therefore, by using a binder which attaches the laser light absorbing particles 4B and the light scattering particles 4A to the surface of the core portion 1A, an adhesion of the surface layer 4 to the core portion 1A is enhanced.

In this case, the binder is preferably made of light transmissible material 4C such as quartz and the like to ensure laser light penetrating in the surface layer 4. On the other hand, laser light transmissible particles having a melting point same to or lower than that of said core portion 1A are used as the transmissible material 4C and they are dispersed together with said absorbing particles 4B and said light scattering particles 4A in a proper liquid such as water. Then the core portion 1A painted with this dispersion, and the emitter is baked at a temperature which is higher than a melting point of the transmissible particle 4C but below the melting point of the core so that the core portion 1A can keep its shape. Accordingly, the transmissible particles 4C melt to form the surface layer of high mechanical strength together with the laser light absorbing particles 4B and the light scattering particles 4A. Therefore, the damage to the emitter surface can be reduced because of the high strength of the surface layer.

Figure 4:
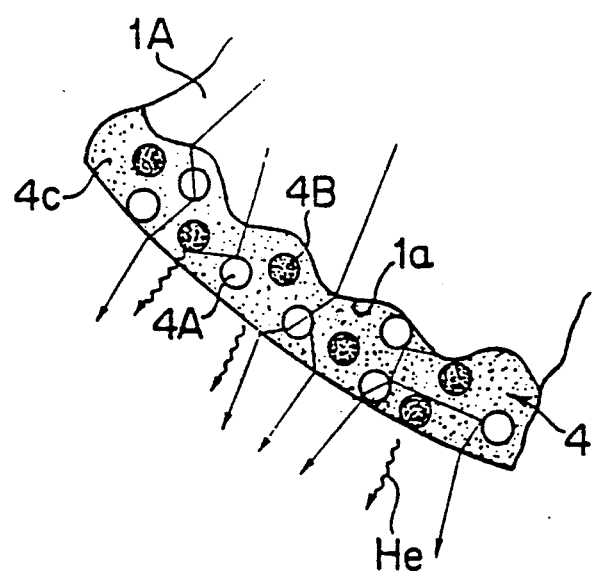

In this case, as shown in FIG. 4, a roughened surface 1a covered with the surface layer 4 is formed on the surface of the core portion 1A enhances an effect of laser light scattering.

The core portion of the optical fiber relating to the present invention is usually fabricated from quartz, but a natural or artificial ceramic material such as diamond, sapphire and the like as well as halogenide glass can be used as the material of the core portion. The diameter of the core portion is preferably 10–1000 μm.

The light scattering particles, having a larger refractive index for the laser light than that of the core portion are of a natural or artificial material such as diamond, sapphire, quartz (a melting point is preferably high), single crystal zirconium oxide ($ZrO_2$), high melting point glass, transmissible and heat resistant synthetic resin, laser light reflective metal, and a particle which is laser light reflective or non-reflective metal particle coated with laser light reflective metal such as gold, aluminum and the like by means of the surface treatment such as gliding.

The transmissible material is preferably made from the transmissible particle which can make a film when it melts and more preferably which has heat resistance such as natural or artificial, sapphire, quartz, glass, transmissible and heat resistant synthetic resin and the like. A suitable transmissible material is selected from these materials in consideration of the relation to the material of the core portion 1A.

The laser light absorbing particle is made of carbon, graphite, iron oxide, manganese dioxide and the any other material which can absorb the laser light to generate heat energy.

A content of each particle in the surface layer (wt %) and each average particle size is preferably within ranges as shown in a following table. More preferable content and particle size are put in parentheses.

| | Content (wt %) | Average Particle Size (μm) |
|---|---|---|
| Light Scattering Particle (A) | 90–1 (70–20) | 0.2–300 (1–50) |
| Absorbing Particle (B) | 90–1 (70–10) | 0.2–500 (1–100) |
| Transmissible Particle (C) | 10–90 (20–50) | 0.2–500 |

The thickness of the surface layer is preferably 10 μm–5 mm, more preferably 30 μm–1 mm. The surface layer is formed as explained hereinafter. If the surface layer can not be formed to be a desired thickness by one step of the method, the step should be repeated until a desired thickness can be obtained;

Said three kinds of particles are dispersed in a dispersion medium, then it is heated to a temperature which is higher than the melting point of the transmissible particle, then the core portion is dipped in the heated dispersion.

Alternatively, said three kinds of particles are melted to be sprayed to the core portion.

Further, other suitable methods for forming the surface layer can be used.

Hereupon, by the above described first method, the dispersion of the three kinds of particles can be painted to the core portion. Moreover, this painting method facilitates the operation, because only the part desired to be covered with the surface layer of the core portion should be dipped in the dispersion and pulled up therefrom. Therefore this method is practical and rational.

As the dispersion medium, suitable liquid such as water, alcohol or a mixture thereof can be used. Further sugar or starch is added to increase the viscosity of the dispersion medium.

As described before, according to the present invention, the forming of the surface layer 4 on the surface of the core portion extends the area of the tissue irradiated by the laser light because the laser light is emitted widely in many directions from the surface layer 4 as shown in FIG. 1.

The inventor has found that when the above described percentage of (B) is high, the incision can be started with a low power level of laser light, then it is possible for the emitter to be moved quickly. However, hemostasis of the treated tissue is reduced. Therefore, the core portion with high percentage of (B) in the surface layer is used effectively for the incision to tissue which can bear damage to some extent such as skin, fat layer and the like.

On the other hand, the core portion with low percentage of (B) is useful to incise tissue for which the hemostasis is to be important such as liver, heart and the like. In this case, the power level of the output from the laser light generator must be raised and the emitter must be moved slowly.

Based on experiments relating to this invention, the inventor introduced these two equations, (1) and (2).

$$\frac{(B)}{(A)+(B)+(C)} \propto \frac{\text{Quantity of laser light for heating}}{\text{Incident laser energy}} \quad (1)$$

$$\frac{(A)+(C)}{(A)+(B)+(C)} \propto \frac{\text{Quantity of laser light for transmitting}}{\text{Incident laser energy}} \quad (2)$$

Equation (1) means that heat generation increased as (B) is increased, then the incision is carried out mainly by evaporation. Therefore, the laser light can not penetrate so deeply into the tissue because most of the incident laser light energy is spent for the heating. As a result, since the incidence of the laser light is not deep in the tissue, the depth of the coagulation layer is reduced.

Equation (2) means that a lot of impinging laser light energy penetrates deeply into the tissue. The tissue absorbing laser light is heated producing coagulation in the tissue.

If a member of laser light emitters which have core portions having different percentages of (B) in the surface layers are prepared in advance, a suitable emitter can be selected in accordance with a current medical purpose, thereby a variety of desired treatments can be carried out.

Figure 11:
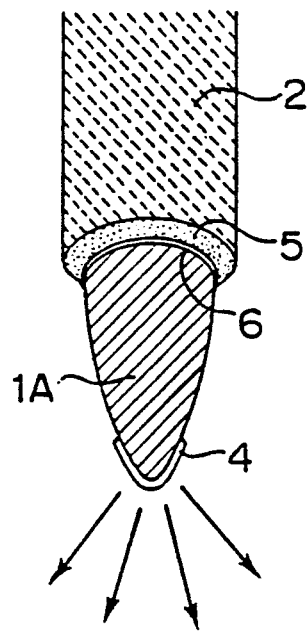
FIG. 11 is a cross sectional view of still other embodiment showing an exposed core portion of a laser light emitter and of forming of a laser light reflection layer relating to the present invention.

As shown in FIG. 11, in order to emit concentratedly the laser light only from the external surface of the core portion 1A, a reflecting layer 6 made by a gilding of gold, aluminium or the like can be formed on the back (holder side) surface of the core portion 1A and/or the concave recess shaped core portion side edge of the holder 2. FIG. 11 shows the reflecting layer 6 formed on the back surface of the core portion 1A. Hereupon, FIG. 11 is a cross sectional view taken on line II—II of FIG. 1 as a different embodiment from that of FIG. 2.

Figure 5:
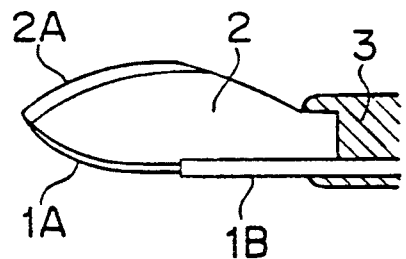
FIGS. 5, 6 and 7 are elevational views of other embodiments of laser light emitters relating to the present invention.
Figure 6:
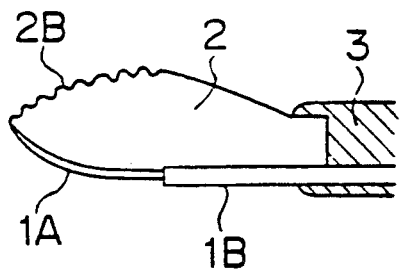

As shown in FIGS. 5 and 6, a knife portion 2A and a cutter portion 2B, which is for stripping in thin sheets, are formed respectively by means of mechanical treatment at an external edge of the holder 2. This edge is opposite to the concave recess shaped core portion side edge of the holder 2. By using such emitters, mechanical incision and stripping in thin sheets of tissue can be carried out as well as the incision by the laser light in the medical treatment.

Figure 7:
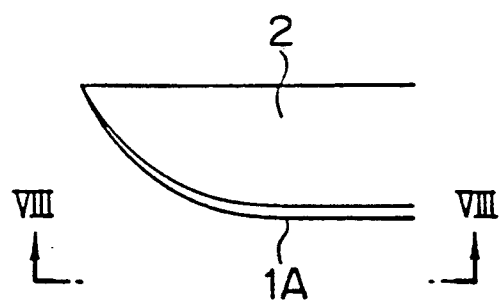
Figure 8:
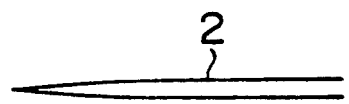
FIG. 8 is a cross sectional view taken on line VIII—VIII of FIG. 7.

In FIGS. 7 and 8, still another embodiment relating to the present invention is shown. According to this embodiment, the core portion 1A is tapered and the holder 2 is the thinner at the nearer part to a tip end of the holder 2. Since the core portion 1A is tapered, it is easy for the emitter to cut into the tissue, and mechanical incision can be included in this incision. Further, even if there is no surface layer on the surface of the core portion 1A, most of the laser light is emitted from the entire surface of the core portion. 1A including the surface of the tapered tip end thereof.

Also as shown in the embodiment of FIG. 1, without the surface layer, the rate of the laser light emission from the bending or curved portion of the core 1A is larger than that from the straight portion of the core portion 1A. As a result, in the present invention, the surface layer is not always necessary due to the bending portion of the core portion 1A.

It is clear that the rate of the laser light emission is increased by the formation of the surface layer in general cases. But, as shown in FIG. 1, even if the surface layer is formed on the entire surface of the core portion 1A there is a small amount of the laser light leaked from the tip end 1b because, the core portion 1A of FIG. 1 is not tapered but keeps constant thickness to the tip end, which is in contrast with the tapered core portion in FIGS. 7 and 8. In order to compensate for leakage of the laser light, a reflecting film made by aluminum gilding and the like can be formed on the tip end.

Figure 9:
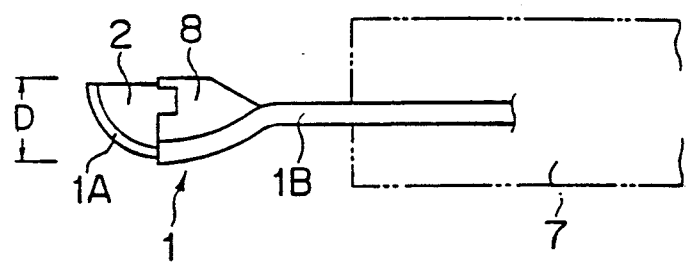
FIGS. 9 and 10 are elevational views of still other embodiments of laser light emitters relating to the present invention.

FIG. 9 shows an embodiment of the laser light emitter of the present invention which is inserted into a tube 7 of an endoscope. A height D of this embodiment is preferably 0.5–4.0 mm. For the incision of this case, a base portion of the optical fiber is repeatedly moved back and forth by an operation outside the tube 7. A fixing piece 8 is also included.

Figure 10:
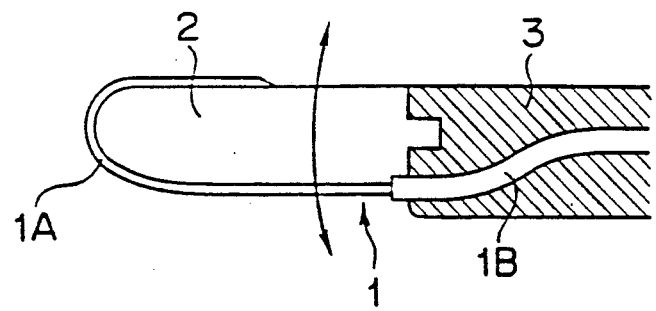

In FIG. 10, the fore end of the holder 2 has a round shape. The core portion 1A extends along the edge of from one external side through the round shape fore end to a part of the other side of the holder 2 and is fixed thereto. Using this emitter, a convex tumor can be incised by the swing of the laser light emitter in the direction of the arrow in FIG. 10. In this case, forming of the surface layer is of no effect.

What is claimed is:
1. A laser light emitter for contact laser surgery comprising:
a holder extending in a longitudinal direction and having a curved edge; and
a clad optical fiber mounted on said holder, at least a section of which is mounted on the curved edge of the holder,
wherein the cladding of the optical fiber is removed from the portion thereof mounted on the curved edge of the holder to form an exposed core section for emission of laser light and for contact with tissue during surgery.

2. A laser light emitter as claimed in claim 1, wherein the holder comprises a heat resistant material having a melting point higher than that of a material of the core of the optical fiber.

3. A laser light emitter as claimed in claim 1, further comprising a hand piece to be held by an operator during surgery, wherein the holder is connected to a fore end of the hand piece, said hand piece supporting a base portion of the optical fiber.

4. A laser light emitter as claimed in claim 1, wherein the exposed core section and at least a portion of the holder taper so as to be thinner at a tip end of the emitter.

5. A laser light emitter as claimed in claim 1, wherein the holder comprises a thin plate having a knife edge at a side opposite to the curved edge.

6. A laser light emitter as claimed in claim 1, further comprising a surface layer covering the exposed core section of said optical fiber, said surface layer containing laser light absorbing particles and laser light scattering particles having a larger refractive index than that of the material of the core.

7. A laser light emitter as claimed in claim 6, wherein said surface layer further contains a binder made from a laser light transmissible material.

8. A laser light emitter as claimed in claim 6, wherein at least part of the exposed core section of the optical fiber is roughened and said surface layer is formed on the roughened part.

9. A laser light emitter as claimed in claim 1, wherein at least one of a surface on the side of exposed core section of the optical fiber in contact with the curved edge of the holder and a surface of the curved edge of the holder is covered with a reflecting layer.

10. A laser light emitter as claimed in claim 1, wherein the holder comprises a thin plate, the fore end of the thin plate having a round shape which forms said curved edge, wherein the exposed core section extends along the curved edge from one external side through the round shaped fore end of a part of the other side of the thin plate and is fixed thereto.

11. A laser light emitter as in claim 1, further comprising a surface layer formed on a light emitting surface of the exposed core section of the fiber, said layer comprising light absorbing particles, said light absorbing particles converting a portion of laser light emitted from the exposed core section to heat for application to the tissue during contact with the tissue during surgery.

12. A laser light emitter as in claim 1, further comprising a surface layer formed on a light emitting surface of the exposed core section of the fiber, said layer comprising scattering particles for scattering a portion of laser light emitted from the exposed core section.

13. A laser light emitter comprising:
an optical fiber having a circular cross section and extending in a longitudinal direction, wherein the fore end portion of said optical fiber has a core which is not surrounded by a clad but is exposed to form a laser light emitting portion; and
a holder comprising a thin plate having a concave recess along a side edge thereof, said optical fiber extending along the inner surface of the concave recess in the side edge of the thin plate and being fixed thereto by a heat resistant adhesive,
wherein part of or the whole of said emitting portion bends at a certain angle on a longitudinal cross section of the extending direction of said optical fiber.

14. A method of irradiating tissue comprising the steps of:
- applying laser light to an optical fiber mounted on a holder;
- emitting the applied laser light from a curving exposed core segment of the fiber which is mounted along a curved edge of the holder;
- contacting the curving exposed core segment with the tissue to be irradiated; and thereby
- applying the emitted light to the tissue.

15. A method of irradiating tissue as in claim 14, further comprising the steps of:
- absorbing a portion of the laser light emitted from the exposed core segment of the fiber in particles contained in a surface layer on the exposed core segment of the fiber, said absorbing converting said portion of laser light to heat; and
- applying the heat together with emitted light to the tissue.

16. A method of irradiating tissue as in claim 15, further comprising the steps of:
- scattering another portion of the laser light emitted from the exposed core segment off second particles contained in the surface layer; and
- applying the scattered light from the surface layer to the tissue.

17. A method of irradiating tissue as in claim 16, further comprising the step of passing a third portion of the laser light emitted from the exposed core segment through a transmissible binder contained in said surface layer.

18. A method of irradiating tissue as in claim 14, further comprising the steps of:
- scattering a portion of the laser light emitted from the exposed core segment off particles contained in a surface layer on the exposed core segment of the fiber; and
- applying the scattered light from the surface layer to the tissue.

* * * * *